(12) United States Patent
Schelberger et al.

(10) Patent No.: US 7,026,315 B1
(45) Date of Patent: Apr. 11, 2006

(54) FUNGICIDE MIXTURES WHICH ARE BASED ON DERIVATIVES OF MORPHOLINE OR PIPERIDINE AND DERIVATIVES OXIME ETHER

(75) Inventors: Klaus Schelberger, Gönnheim (DE); Maria Scherer, Landau (DE); Reinhold Saur, Böhl-Iggelheim (DE); Karl Eicken, Wachenheim (DE); Egon Haden, Kleinniedesheim (DE); Eberhard Ammermann, Heppenheim (DE); Thomas Grote, Schifferstadt (DE); Gisela Lorenz, Neustadt (DE); Siegfried Strathmann, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/868,515

(22) PCT Filed: Dec. 11, 1999

(86) PCT No.: PCT/EP99/09803

§ 371 (c)(1),
(2), (4) Date: Jun. 18, 2001

(87) PCT Pub. No.: WO00/36917

PCT Pub. Date: Jun. 29, 2000

(30) Foreign Application Priority Data

Dec. 19, 1998 (DE) .................... 198 58 911

(51) Int. Cl.
| | | |
|---|---|---|
| *A61K 31/535* | (2006.01) | |
| *A61K 31/15* | (2006.01) | |
| *A61K 31/165* | (2006.01) | |
| *A61K 31/435* | (2006.01) | |
| *A61K 31/335* | (2006.01) | |

(52) U.S. Cl. .................. 514/231.2; 514/640; 514/617; 514/277; 514/467

(58) Field of Classification Search ............ 514/231.5, 514/640, 231.2, 617, 277, 467
See application file for complete search history.

(56) References Cited

U.S. PATENT DOCUMENTS 4,851,405 A  7/1989  Kramer
5,972,941 A  10/1999  Schwalge

FOREIGN PATENT DOCUMENTS

| EP | 281 842 | 9/1988 |
| EP | 919 126 | 6/1999 |
| WO | WO 9619442 | * 6/1996 |
| WO | 97/06681 | 2/1997 |

* cited by examiner

*Primary Examiner*—Shaojia Anna Jiang
(74) *Attorney, Agent, or Firm*—Novak Druce & Quigg, LLP

(57) ABSTRACT

Fungicidal mixtures, comprising as active components
a) a morpholine or piperidine derivative I selected from the group of the compounds Ia, Ib, Ic and Id

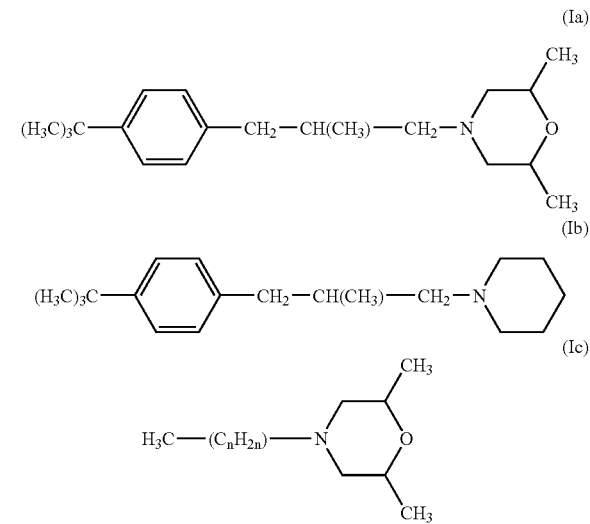

[n = 10, 11, 12 (60–70%) or 13]

and
b) compounds of the formula II

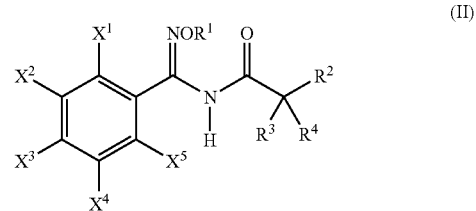

in a synergistically effective amount are described.

21 Claims, No Drawings

FUNGICIDE MIXTURES WHICH ARE BASED ON DERIVATIVES OF MORPHOLINE OR PIPERIDINE AND DERIVATIVES OXIME ETHER

This application is a 371 of PCT/EP99/09803 filed Dec. 11, 1999 which claims foreign priority to Germany 198589115 under 35 U.S.C. 119(a)–(d), filed Dec. 19, 1998.

The present invention relates to fungicidal mixtures for controlling harmful fungi and to methods for controlling harmful fungi using such mixtures.

WO 97/40673 provides fungicidal mixtures which, inter alia, comprise active compounds of the formulae Ia, Ib and/or Ic in addition to other fungicidally active compounds from the group of the oxime ethers and/or the carbamates.

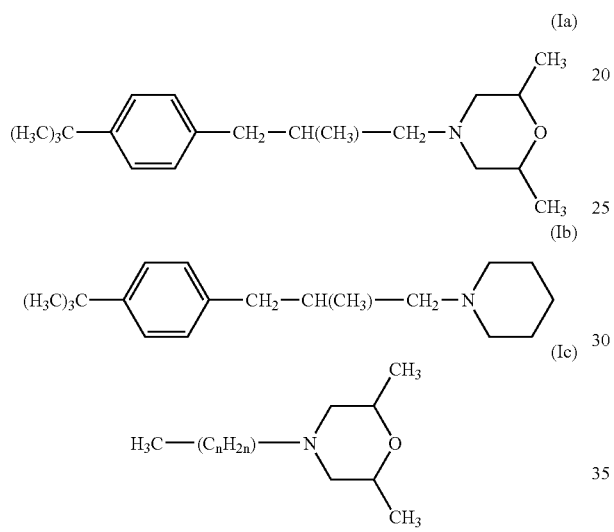

[n = 10, 11, 12 (60–70%) or 13]

Other fungicidal mixtures which comprise active compounds of the formulae Ia to Ic are disclosed in EP-A 797386, WO 97/06681, EP-B 425857, EP-B 524496, EP-A 690792, WO 94/22308 and EP-B 645087.

Brighton Crop Protection Conference 1996, Pests and Diseases, pp. 47–52 discloses the active compound of the formula Id:

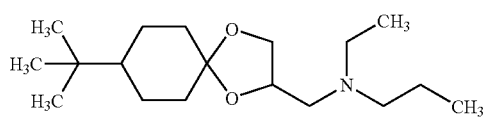

DE 19722223 describes mixtures of compounds of the formula II and of active compounds from the class of the strobilurins.

It is an object of the present invention to provide other particularly effective mixtures for controlling harmful fungi and, in particular, for certain indications.

We have found that this object is surprisingly achieved with a mixture which, as active compounds, comprises morpholine or piperidine derivatives of the formula I defined at the outset and, as further fungicidally active component, at least one fungicidally active compound of the formula II

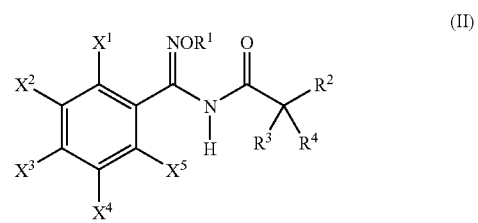

where the substituents $X^1$ to $X^5$ and $R^1$ to $R^4$ are as defined below:

$X^1$ is $C_1$-$C_4$-haloalkyl, $C_1$-$C_4$-haloalkoxy or halogen $X^2$ to $X^5$ are, independently of one another, hydrogen, halogen, $C_1$-$C_4$-alkyl, $C_1$-$C_4$-haloalkyl, $C_1$-$C_4$-alkoxy or $C_1$-$C_4$-haloalkoxy;

$R^1$ is $C_1$-$C_4$alkyl, $C_2$-$C_6$-alkenyl, $C_2$-$C_6$-alkynyl, $C_1$-$C_4$-alkyl-$C_3$-$C_7$-cycloalkyl, where these radicals may carry substituents selected from the group consisting of halogen, cyano and $C_1$-$C_4$-alkoxy, $R^2$ is a phenyl radical or a 5- or 6-membered saturated or unsaturated heterocyclyl radical having at least one heteroatom selected from the group consisting of N, O and S, where the cyclic radicals may have one to three substituents selected from the group consisting of halogen, $C_1$-$C_4$-alkyl, $C_1$-$C_4$-alkoxy-$C_2$-$C_4$-alkenyl, $C_1$-$C_4$-alkoxy-$C_2$-$C_4$-alkynyl, $R^3$ and $R^4$ are, independently of one another, hydrogen, $C_1$-$C_4$-alkyl, $C_1$-$C_4$-alkoxy, $C_1$-$C_4$-alkylthio, N-$C_1$-$C_4$-alkylamino, $C_1$-$C_4$-haloalkyl or $C_1$-$C_4$-haloalkoxy in a synergistically effective amount.

The mixtures according to the invention act synergistically, and they are therefore particularly suitable for controlling harmful fungi and, in particular, powdery mildew fungi.

In the context of the present invention, halogen is fluorine, chlorine, bromine and iodine and in particular fluorine, chlorine and bromine.

The term "alkyl" includes straight-chain and branched alkyl groups. These are preferably straight-chain or branched $C_1$-$C_{12}$-alkyl groups and in particular $C_1$-$C_6$-alkyl groups. Examples of alkyl groups are alkyl, such as, in particular, methyl, ethyl, propyl, 1-methylethyl, butyl, 1-methylpropyl, 2-methylpropyl [lacuna] 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 1-methylhexyl, 1-ethylpentyl, 2-ethylpentyl, 1-propylbutyl, octyl, decyl, dodecyl.

Haloalkyl is an alkyl group which is defined as above and is partially or fully halogenated by one or more halogen atoms, in particular by fluorine and chlorine. Preferably, there are 1 to 3 halogen atoms present, and particular preference is given to the difluoromethyl and the trifluoromethyl group.

The alkenyl group includes straight-chain and branched $C_2$-$C_6$-alkenyl groups. Examples of alkenyl groups are 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3- butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl, in particular 2-propenyl, 2-butenyl, 3-methyl-2-butenyl and 3-methyl-2-pentenyl.

The alkenyl group may be partially or fully halogenated by one or more halogen atoms, in particular by fluorine and chlorine. It has preferably 1 to 3 halogen atoms.

The alkynyl group includes straight-chain and branched $C_3$-$C_6$-alkynyl groups. Examples of alkynyl groups are 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-alkynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,2-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl.

The $C_1$-$C_4$-alkylene-$C_3$-$C_7$-cycloalkyl group is a $C_3$-$C_7$-cycloalkyl group, such as cyclopropyl, cyclobutyl, cyclopentyl or cyclohexyl, which is attached via a $C_1$-$C_4$-alkylene radical.

Suitable substituents $R^2$ are, in addition to phenyl (unsubstituted or substituted), in particular thienyl, pyrazolyl, pyrrolyl, imidazolyl, thiazolyl, furyl, pyridazinyl and pyrimidinyl. Preferred substituents at these ring systems are halogen (in particular F and Cl), $C_1$-$C_4$-alkoxy (in particular methoxy) and $C_1$-$C_4$-alkyl (in particular methyl, ethyl). The number of the ring substituents can be from 1 to 3 and is in particular 1 or 2. Particular preference is given to phenyl or substituted phenyl, thienyl, thienyl-$C_1$-$C_4$-alkyl, pyrazolyl and pyrazol-$C_1$-$C_4$-alkyl.

The substituents $R^3$ and $R^4$ are $C_1$-$C_4$-alkyl, $C_1$-$C_4$-alkoxy, $C_1$-$C_4$-alkylthio, N-$C_1$-$C_4$-alkylamino, $C_1$-$C_4$-haloalkyl or $C_1$-$C_4$-haloalkoxy. Preferred substituents $R^3$ and $R^4$ are hydrogen, F, Cl, methyl, ethyl, methoxy, thiomethyl and N-methylamino. $R^3$ and $R^4$ together may also form a grouping =O.

The morpholin or piperidine derivatives I (Ia: common name: Fenpropimorph, U.S. Pat. No. 4,202,894; Ib: common name: Fenpropidin, U.S. Pat. No. 4,202,894; Ic: common name: Tridemorph, DE-A 11 64 152), their preparation and their action against harmful fungi are known, and they are commercially available products.

The compounds of the formula II and processes for their preparation are described in WO-A 96/10442 and in the earlier applications DE 1 97 41098.7 and 1 97 41099.5.

Among the compounds of the formula II, preference is given to those where $X^1$ is a $C_1$-$C_4$-haloalkyl, in particular a trifluoromethyl group, a $C_1$-$C_4$-haloalkoxy, in particular a difluoromethoxy or trifluoromethoxy group or a halogen, in particular chlorine and $X^2$ and $X^3$ are a hydrogen atom or a halogen group, in particular a hydrogen atom. $X^4$ and $X^5$ are preferably hydrogen, halogen (in particular Cl or F), $C_1$-$C_4$-alkoxy (in particular methoxy or ethoxy), $C_1$-$C_4$-haloalkyl (in particular trifluoromethyl) or $C_1$-$C_4$-haloalkoxy (in particular trifluoromethoxy).

Preferred substituents $R^1$ are $C_1$-$C_4$-alkyl (methyl, ethyl, n- and isopropyl and t-butyl), $C_1$-$C_4$-alkylene-$C_3$-$C_7$-cycloalkyl, $C_1$-$C_4$-alkenyl (in particular ethenyl, propenyl and butenyl, which may be substituted, in particular by halogen (preferably Cl)), propynyl, cyanomethyl and methoxymethyl. Among the $C_1$-$C_4$-alkylene-$C_3$-$C_7$-cycloalkyl substituents, methylene-substituted compounds, in particular emthylenecyclopropyl, methylenecyclopentyl, methylenecyclohexyl and methylenecyclohexenyl, are particularly preferred. The rings in these substituents may be substituted, preferably by halogen.

Suitable substituents $R^2$ are, in addition to phenyl (unsubstituted or substituted), in particular thienyl, pyrazolyl, pyrrolyl, imidazolyl, thiazolyl, furyl, pyridazinyl and pyrimidinyl. Preferred substituents at these ring systems are halogen (in particular F and Cl), $C_1$-$C_4$alkoxy (in particular methoxy) and $C_1$-$C_4$-alkyl (in particular methyl, ethyl). The number of the ring substituents can be from 1 to 3 and is in particular 1 or 2. Particular preference is given to phenyl or substituted phenyl.

Preferred compounds of the formula II are shown, in the tables of WO 96/019442, which has already been mentioned. Among these compounds, in turn, particular preference is given to the compounds listed in Table 1 below ($R^3$ and $R^4$ are each hydrogen).

TABLE 1

| No. | $X^1$ | $X^2$ | $X^3$ | $X^4$ | $X^5$ | $R^1$ | $R^2$ |
|---|---|---|---|---|---|---|---|
| II.1 | $CF_3$ | H | H | H | H | ethyl | Ph-4-OMe |
| II.2 | $CF_3$ | H | H | H | H | methyl | Ph-4-OMe |
| II.3 | $CF_3$ | H | H | H | H | —$CH_2$-cPr | 2-thienyl |
| II.4 | $CF_3$ | H | H | H | H | —$CH_2$-cPr | 3-thienyl |
| II.5 | $CF_3$ | H | H | H | H | —$CH_2$-cPr | Ph-2,4-$F_2$ |
| II.6 | $CF_3$ | H | H | H | H | —$CH_2$-cPr | Ph-2-F |
| II.7 | $CF_3$ | H | H | H | H | —$CH_2$-cPr | Ph-2-F-4-OMe |
| II.8 | $CF_3$ | H | H | H | H | —$CH_2$-cPr | Ph-3-Me |
| II.9 | $CF_3$ | H | H | H | H | —$CH_2$-cPr | Ph-3-Me-4-OMe |
| II.10 | $CF_3$ | H | H | H | H | —$CH_2$-cPr | Ph-4-F |
| II.11 | $CF_3$ | H | H | H | H | —$CH_2$-cPr | Ph-4-Me |
| II.12 | $CF_3$ | H | H | H | H | —$CH_2$-cPr | Ph-4-OMe |
| II.13 | $CF_3$ | H | H | H | H | —$CH_2$-cPr | Ph |
| II.14 | $CF_3$ | H | H | H | H | —$CH_2$—CH=$CH_2$ | Ph |

TABLE 1-continued

| No. | $X^1$ | $X^2$ | $X^3$ | $X^4$ | $X^5$ | $R^1$ | $R^2$ |
|---|---|---|---|---|---|---|---|
| II.15 | $CF_3$ | H | H | H | H | —$CH_2$—CH=$CH_2$ | Ph-4-OMe |
| II.16 | $CF_3$ | H | H | H | H | —$CH_2$—CH=$CCl_2$ | Ph-4-OMe |
| II.17 | $CF_3$ | H | H | H | F | —$CH_2$—$CH_3$ | Ph-4-OMe |
| II.18 | $CF_3$ | H | H | H | F | —$CH_2CH_3$ | Ph |
| II.19 | $CF_3$ | H | H | H | F | —$CH_3$ | Ph-4-OMe |
| II.20 | $CF_3$ | H | H | H | F | —$CH_2$-cPr | Ph |
| II.21 | $CF_3$ | H | H | H | F | —$CH_2$-cPr | Ph-2-F |
| II.22 | $CF_3$ | H | H | H | F | —$CH_2$-cPr | Ph-2,4-$F_2$ |
| II.23 | $CF_3$ | H | H | H | F | —$CH_2$-cPr | Ph-2-F-3-Me |
| II.24 | $CF_3$ | H | H | H | F | —$CH_2$-cPr | Ph-2-F-4-OMe |
| II.25 | $CF_3$ | H | H | H | F | —$CH_2$-cPr | Ph-3,5-$Me_2$ |
| II.26 | $CF_3$ | H | H | H | F | —$CH_2$-cPr | 3-methylpyrazol-1-yl |
| II.27 | $CF_3$ | H | H | H | F | —$CH_2$-cPr | 3-methyl-2-thienyl |
| II.28 | $CF_3$ | H | H | H | F | —$CH_2$-cPr | 2-thienyl |
| II.29 | $CF_3$ | H | H | H | F | —$CH_2$-cPr | 3-thienyl |
| II.30 | $CF_3$ | H | H | H | F | —$CH_2$—$CHF_2$ | Ph-4-OMe |
| II.31 | $CF_3$ | H | H | H | F | —$CH_2$—$OCH_3$ | Ph-4-OMe |
| II.32 | $CF_3$ | H | H | H | F | —$CH_2$—$OCH_3$ | Ph |
| II.33 | $CF_3$ | H | H | H | F | —$CH_2CN$ | Ph-4-Ome |
| II.34 | $CF_3$ | H | H | H | F | —$CH_2CN$ | Ph |
| II.35 | $CF_3$ | H | H | H | F | —$CH_2$—C≡CH | Ph |
| II.36 | $CF_3$ | H | H | H | F | —$CH_2$—C≡CH | Ph-4-OMe |
| II.37 | $CF_3$ | H | H | H | F | —$CH_2$—C≡CH | Ph-2-F |
| II.38 | $CF_3$ | H | H | H | F | —$CH_2$—C≡CH | Ph-4-Me |
| II.39 | $CF_3$ | H | H | H | F | —$CH_2$—C≡CH | 2-thienyl |
| II.40 | $CF_3$ | H | H | H | F | —$CH_2$—C≡CH | Ph-2-F-4-OMe |
| II.41 | $CF_3$ | H | H | H | F | i-propyl | Ph |
| II.42 | $CF_3$ | H | H | H | F | n-butyl | Ph |
| II.43 | $CF_3$ | H | H | H | F | n-propyl | Ph |
| II.44 | $CF_3$ | H | H | H | F | t-butyl | Ph |
| II.45 | $CF_3$ | H | H | H | Cl | —$CH_3$ | |
| II.46 | $CF_3$ | H | H | H | Cl | —$CH_2CN$ | Ph-4-OMe |
| II.47 | $CF_3$ | H | H | H | Cl | —$CH_2$—OMe | Ph-4-OMe |
| II.48 | $CF_3$ | H | H | H | Cl | —$CH_2$-cPr | Ph |
| II.49 | $CF_3$ | H | H | H | Cl | —$CH_2$-cPr | 3-methylpyrazol-1-yl |
| II.50 | $CF_3$ | H | H | H | Cl | —$CH_2$-cPr | 2-thienyl |
| II.51 | $CF_3$ | H | H | H | Cl | —$CH_2$-cPr | Ph-2,4-$F_2$ |
| II.52 | $CF_3$ | H | H | H | Cl | —$CH_2$—C≡CH | Ph-4-OMe |
| II.53 | $CF_3$ | H | H | H | $CF_3$ | —$CH_3$ | Ph-4-OMe |
| II.54 | $CF_3$ | H | H | H | $CF_3$ | —$CH_2CH_2Cl$ | Ph-4-OMe |
| II.55 | $CF_3$ | H | H | H | $CF_3$ | —$CH_2$-cPr | 2-thienyl |
| II.56 | $CF_3$ | H | H | H | $CF_3$ | —$CH_2$-cPr | Ph-2-F-5-Me |
| II.57 | $CF_3$ | H | H | H | $CF_3$ | —$CH_2$-cPr | Ph-4-OMe |
| II.58 | $CF_3$ | H | H | H | $CF_3$ | —$CH_2$-cPr | Ph |
| II.59 | $CF_3$ | H | H | H | $OCH_3$ | —$CH_2CH_3$ | Ph-4-OMe |
| II.60 | $CF_3$ | H | H | H | $OCH_3$ | —$CH_2$-cPr | Ph-4-OMe |
| II.61 | $CF_3$ | H | H | H | $OCH_3$ | —$CH_2$-cPr | Ph |
| II.62 | $CF_3$ | H | H | Cl | F | —$CH_2$—$CH_2Cl$ | Ph |
| II.63 | $CF_3$ | H | H | Cl | F | —$CH_2$—CH=$CH_2$ | Ph-4-OMe |
| II.64 | $CF_3$ | H | H | Cl | F | —$CH_2$-cPr | 2-thienyl |
| II.65 | $CF_3$ | H | H | Cl | F | —$CH_2$-cPr | Ph-2-F |
| II.66 | $CF_3$ | H | H | Cl | F | —$CH_2$-cPr | Ph |
| II.67 | $CF_3$ | H | H | Cl | F | —$CH_2$-cPr | Ph-2-F-5-Me |
| II.68 | $CF_3$ | H | H | Cl | Cl | —$CH_2$—CH=$CH_2$ | Ph-4-OMe |
| II.69 | $CF_3$ | H | H | Cl | Cl | —$CH_2CH_2Cl$ | Ph |
| II.70 | $CF_3$ | H | H | Cl | Cl | —$CH_2CH_3$ | Ph-2-F-5-Me |
| II.71 | $CF_3$ | H | H | Cl | Cl | —$CH_2$-cPr | Ph-3,5-$Me_2$ |
| II.72 | $CF_3$ | H | H | $SCH_3$ | F | —$CH_2$-cPr | Ph-4-OMe |
| II.73 | $CF_3$ | H | H | $OCH_3$ | F | —$CH_2$-cPr | Ph-4-OMe |
| II.74 | $CF_3$ | H | F | H | H | —$CH_2$-cPr | Ph |
| II.75 | $CF_3$ | H | F | H | H | —$CH_2$—$CH_3$ | Ph-4-OMe |
| II.76 | $CF_3$ | H | H | F | F | —$CH_2CH_3$ | Ph |
| II.77 | $CF_3$ | H | H | F | F | —$CH_2$—$CH_2Cl$ | Ph-2-F-5-Me |
| II.78 | $CF_3$ | H | H | F | F | —$CH_2$—$OCH_3$ | Ph-4-OMe |
| II.79 | $CF_3$ | H | H | F | F | —$CH_2$-cPr | Ph |
| II.80 | $CF_3$ | H | H | F | F | —$CH_2$-cPr | 3-methylpyrazol-1-yl |
| II.81 | $CF_3$ | H | H | F | F | —$CH_2$-cPr | 3-methyl-2-thienyl |
| II.82 | $CF_3$ | H | H | F | F | —$CH_2$-cPr | Ph-2-F-3-Me |
| II.83 | $CF_3$ | H | H | F | F | —$CH_2$-cPr | Ph-2-F-4-OMe |
| II.84 | $CF_3$ | H | H | F | F | —$CH_2$-cPr | Ph-2-F-5-Me |
| II.85 | $CF_3$ | H | H | F | F | —$CH_2$-cPr | Ph-4-OMe |
| II.86 | $CF_3$ | H | H | F | F | —$CH_2$-cPr | Ph-4F |

TABLE 1-continued

| No. | X¹ | X² | X³ | X⁴ | X⁵ | R¹ | R² |
|---|---|---|---|---|---|---|---|
| II.87 | $CF_3$ | H | H | F | F | i-propyl | Ph-4-OMe |
| II.88 | $CF_3$ | H | H | F | F | n-butyl | Ph-4-OMe |
| II.89 | $CF_3$ | H | H | F | F | —$CH_2$—C≡CH | Ph-4-OMe |
| II.90 | $CF_3$ | H | H | $CF_3$ | F | —$CH_3$ | Ph-4-OMe |
| II.91 | $CF_3$ | H | H | $CF_3$ | F | —$CH_2$—CH=$CH_2$ | Ph |
| II.92 | $CF_3$ | H | H | $CF_3$ | F | —$CH_2$-cPr | Ph |
| II.93 | $CF_3$ | H | H | Cl | Cl | —$CH_2$-cHxe-3 | Ph |
| II.94 | $CF_3$ | H | H | F | H | —$CH_2$-cPr | Ph-4-F |
| II.95 | $CF_3$ | H | H | Cl | Cl | —$CH_2$-cHex | Ph |
| II.96 | $CF_3$ | H | H | H | F | —$CH_2$—$SCH_3$ | Ph |
| II.97 | $CF_3$ | H | H | H | F | —$CH_2$—$SOCH_3$ | Ph |
| II.98 | $CF_3$ | H | H | H | F | —$CH_2$—$SO_2CH_3$ | Ph |
| II.99 | $CF_3$ | H | H | H | F | —$CH_2$—NHMe | Ph |
| II.100 | $CF_3$ | H | H | H | F | $CH_2$—$CONH_2$ | Ph |
| II.101 | $CF_3$ | H | H | H | F | $CH_2CON(CH_3)_2$ | Ph |

In the table above, cPr is cyclopropyl, cHxe-n is cyclohexenyl which is unsaturated in position n, c-Hex is cyclohexyl and Ph is phenyl.

Particular preference is given to compounds II in which $R^1$ is a radical $CH_2$-cPr and $R^2$ is an unsubstituted or substituted phenyl radical. Among these, in turn, preference is given to the compounds in which $X^4$ and X5 [sic] are halogen, preferably F.

Other preferred compounds of the formula II are shown in Tables 2 and 3 below.

TABLE 2

Compounds of the formula II'

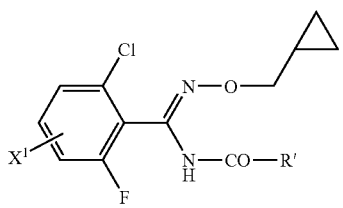

(II')

where the substituents are as defined below:

| No. | X¹ | R' | m.p. (° C.) |
|---|---|---|---|
| II.102 | H | 4-$CH_3$—$C_6H_4$—$CH_2$ | 86–88 |
| II.103 | H | 4-F—$C_6H_4$—$CH_2$ | 79–81 |
| II.104 | H | 4-Cl—$C_6H_4$—$CH_2$ | 105–107 |
| II.105 | H | 4-$CH_3O$—$C_6H_4$—$CH_2$ | 73–76 |
| II.106 | H | 4-$CF_3$—$C_6H_4$—$CH_2$ | |
| II.107 | 5-F | 4-$CH_3$—$C_6H_4$—$CH_2$ | 87–90 |
| II.108 | 5-F | 4-F—$C_6H_4$—$CH_2$ | 71–74 |
| II.109 | 5-F | 4-Cl—$C_6H_4$—$CH_2$ | 85–87 |
| II.110 | 5-F | 4-$CH_3O$—$C_6H_4$—$CH_2$ | 90–92 |
| II.111 | 5-F | 4-$CF_3$—$C_6H_4$—$CH_2$ | |
| II.112 | H | 2-thienylmethyl | 87–89 |
| II.113 | H | 3-thienylmethyl | |
| II.114 | 5-F | 2-thienylmethyl | 90–93 |
| II.115 | 5-F | 3-thienylmethyl | |
| II.116 | 5-F | 3-$CH_3$—$C_6H_4$—$CH_2$ | 72–75 |
| II.117 | 5-F | 2-F—$C_6H_4$—$CH_2$ | 73–76 |
| II.118 | 5-F | 4-$CH_2FO$—$C_6H_4$—$CH_2$ | oil |

TABLE 3

Compounds of the formula II''

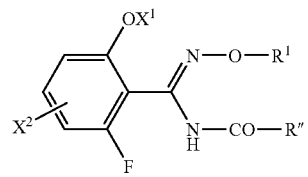

(II'')

| No. | OX¹ | X² | R¹ | R'' | m.p. ° C. |
|---|---|---|---|---|---|
| II.119 | $CHF_2$ | H | $C_2H_5$ | $C_6H_5$—$CH_2$ | |
| II.120 | $CHF_2$ | H | $C_2H_5$ | 4-$CH_3O$—$C_6H_4$—$CH_2$ | |
| II.121 | $CHF_2$ | H | $CH_2$—CH=$CH_2$ | $C_6H_5$—$CH_2$ | |
| II.122 | $CHF_2$ | H | $CH_2$—C≡CH | $C_6H_5$—$CH_2$ | |
| II.123 | $CHF_2$ | H | $CH_2$—C≡CH | 4-$CH_3O$—$C_6H_4$—$CH_2$ | |
| II.124 | $CHF_2$ | H | cPr | $C_6H_5$—$CH_2$ | |
| II.125 | $CF_3$ | H | cPr | $C_6H_5$—$CH_2$ | |
| II.126 | $CHF_2$ | H | cPr | 4-F—$C_6H_4$—$CH_2$ | 75–77 |
| II.127 | $CHF_2$ | H | cPr | 4-Cl—$C_6H_4$—$CH_2$ | 81–83 |
| II.128 | $CHF_2$ | H | cPr | 4-$CH_3O$—$C_6H_4$—$CH_2$ | 57–59 |
| II.129 | $CHF_2$ | H | cPr | 4-$CF_3$—$C_6H_4$—$CH_2$ | |
| II.130 | $CHF_2$ | H | cPr | 2-thienylmethyl | oil |
| II.131 | $CHF_2$ | H | cPr | 3-thienylmethyl | oil |
| II.132 | $CHF_2$ | H | cPr | pyrazolyl-1-methyl | |
| II.133 | $CHF_2$ | H | cPr | 4-$CH_3$—$C_6H_4$—$CH_2$ | |
| II.134 | $CHF_2$ | 5-F | $CH_2$—CH=$CH_2$ | $C_6H_5$—$CH_2$ | |
| II.135 | $CHF_2$ | 5-F | $CH_2$—CH=$CH_2$ | 4-$CH_3O$—$C_6H_4$—$CH_2$ | |
| II.136 | $CHF_2$ | 5-F | $CH_2$—C≡CH | $C_6H_5$—$CH_2$ | |
| II.137 | $CHF_2$ | 5-F | $CH_2$—C≡CH | 4-$CH_3O$—$C_6H_4$—$CH_2$ | |
| II.139 | $CHF_2$ | 5-F | cPr | 4-F—$C_6H_4$—$CH_2$ | 64–67 |
| II.140 | $CHF_2$ | 5-F | cPr | 4-Cl—$C_6H_4$—$CH_2$ | 72–75 |
| II.141 | $CHF_2$ | 5-F | cPr | 4-$CH_3$—$C_6H_4$—$CH_2$ | 74–76 |
| II.142 | $CHF_2$ | 5-F | cPr | 4-$CH_3O$—$C_6H_4$—$CH_2$ | 79–81 |
| II.143 | $CHF_2$ | 5-F | cPr | 4-$CF_3$—$C_6H_4$—$CH_2$ | |
| II.144 | $CF_3$ | 5-F | cPr | $C_6H_5$—$CH_2$ | |
| II.145 | $CHF_2$ | 4-F | cPr | $C_6H_5$—$CH_2$ | |
| II.146 | $CHF_2$ | 4-F | cPr | 4-$CH_3O$—$C_6H_4$—$CH_2$ | |
| II.147 | $CHF_2$ | H | cPr | 4-$CH_3$—$C_6H_4$—$CH_2$ | 69–71 |

The physical data of these compounds and processes for their preparation are given in the already mentioned WO 96/19442, DE 197441098.7 and DE 19741099.5.

The ratios of the compounds I and II can be varied within wide ranges; the active compounds are preferably employed in a ratio by weight in the range from 20:1 to 1:20, in particular 10:1 to 1:10.

When preparing the mixtures, it is preferred to employ the pure active ingredients I and II, to which further active ingredients against harmful fungi or other pests, such as insects, arachnids or nematodes, or else herbicidal or growth-regulating active ingredients or fertilizers can be admixed.

The mixtures of the compounds I and II, or the compounds I and II used simultaneously, jointly or separately, exhibit outstanding activity against a wide range of phytopathogenic fungi, in particular from the classes of the Ascomycetes, Basidiomycetes, Phycomycetes and Deuteromycetes. Some of them act systemically and can therefore be employed as foliar- and soil-acting fungicides.

They are especially important for controlling a large number of fungi in a variety of crop plants, such as cotton, vegetable species (e.g. cucumbers, beans, tomatoes, potatoes and cucurbits), barley, grass, oats, bananas, coffee, maize, fruit species, rice, rye, soya, grapevine, wheat, ornamentals, sugar cane, and a variety of seeds.

They are particularly suitable for controlling the following phytopathogenic fungi: *Erysiphe graminis* (powdery mildew) in cereals, *Erysiphe cichoracearum* and *Sphaerotheca fuliginea* in cucurbits, *Podosphaera leucotricha* in apples, *Uncinula necator* in grapevines, *Puccinia* species in cereals, *Rhizoctonia* species in cotton, rice and lawns, *Ustilago* species in cereals and sugar cane, *Venturia inaequalis* (scab) in apples, *Helminthosporium* species in cereals, *Septoria nodorum* in wheat, *Botrytis cinera* (gray mold) in strawberries, vegetables, ornamentals and grapevines, *Cercospora arachidicola* in groundnuts, *Pseudocercosporella herpotrichoides* in wheat and barley, *Pyricularia oryzae* in rice, *Phytophthora infestans* in potatoes and tomatoes, *Plasmopara viticola* in grapevines, *Pseudoperonospora* species in hops and cucumbers, *Alternaria* species in vegetables and fruit, *Mycosphaerella* species in bananas and *Fusarium* and *Verticillium* species.

They can furthermore be employed in the protection of materials (for example the protection of wood), for example against *Paecilomyces variotii*.

The compounds I and II can be applied simultaneously, that is either together or separately, or successively, the sequence, in the case of separate application, generally not having any effect on the result of the control measures.

Depending on the kind of effect desired, the application rates of the mixtures according to the invention are, in particular in agricultural crop areas, from 0.01 to 10 kg/ha, preferably 0.1 to 5 kg/ha, in particular 0.2 to 3.0 kg/ha.

The application rates of the compounds I are from 0.01 to 2.5 kg/ha, preferably 0.01 to 10 kg/ha, in particular 0.05 to 5.0 kg/ha.

Correspondingly, in the case of the compounds II, the application rates are from 0.01 to 2 kg/ha, preferably 0.02 to 2 kg/ha, in particular 0.02 to 1.0 kg/ha.

For seed treatment, the application rates of the mixture are generally from 0.001 to 250 g/kg of seed, preferably 0.01 to 100 g/kg, in particular 0.01 to 50 g/kg.

If phytopathogenic harmful fungi are to be controlled, the separate or joint application of the compounds I and II or of the mixtures of the compounds I and II is effected by spraying or dusting the seeds, the plants or the soils before or after sowing of the plants, or before or after plant emergence.

The fungicidal synergistic mixtures according to the invention or the compounds I and II can be formulated for example in the form of ready-to-spray solutions, powder and suspensions or in the form of highly concentrated aqueous, oily or other suspensions, dispersions, emulsions, oil dispersions, pastes, dusts, materials for broadcasting or granules, and applied by spraying, atomizing, dusting, broadcasting or watering. The use form depends on the intended purpose; in any case, it should ensure as fine and uniform as possible a distribution of the mixture according to the invention.

The formulations are prepared in a known manner, e.g. by extending the active compound with solvents and/or carriers, if desired using emulsifiers and dispersants, it being possible also to use other organic solvents as auxiliary solvents if water is used as the diluent. Suitable auxiliaries for this purpose are essentially: solvents such as aromatics (e.g. xylene), chlorinated aromatics (e.g. chlorobenzenes), paraffins (e.g. mineral oil fractions), alcohols (e.g. methanol, butanol), ketones (e.g. cyclohexanone), amines (e.g. ethanolamine, dimethylformamide) and water; carries such as ground natural minerals (e.g. kaolins, clays, talc, chalk) and ground synthetic minerals (e.g. finely divided silica, silicates); emulsifiers such as nonionic and anionic emulsifiers (e.g. polyoxyethylene fatty alcohol ethers, alkylsulfonates and arylsulfonates) and dispersants such as lignosulfite waste liquors and methylcellulose.

Suitable surfactants are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols, or of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenol or tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene, lauryl alcohol polyglycol ether acetate, sorbitol esters, lignosulfite waste liquors or methylcellulose.

Powders and materials for broadcasting and dusts can be prepared by mixing or jointly grinding the compounds I or II or the mixture of the compounds I and II with a solid carrier.

Granules (e.g. coated granules, impregnated granules or homogeneous granules) are usually prepared by binding the active compound, or active compounds, to a solid carrier.

Fillers or solid carriers are, for example, mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials and fertilizers, such as ammonium sulfate, ammonium phosphate, ammonium nitrate, ureas, and products of vegetable origin, such as cereal meal, tree bark meal, wood meal and nutshell meal, cellulose powders or other solid carriers.

The formulations generally comprise from 0.1 to 95% by weight, preferably 0.5 to 90% by weight, of one of the compounds I or II or of the mixture of the compounds I and II. The active compounds are employed in a purity of from 90% to 100%, preferably 95% to 100% (according to NMR spectrum or HPLC spectrum [sic]).

The compounds I or II, the mixtures, or the corresponding formulations, are applied by treating the harmful fungi, their habitat, or the plants, seeds, soils, areas, materials or spaces to be kept free from them with a fungicidally effective amount of the mixture, or of the compounds I and II in the case of separate application.

Application can be effected before or after infection by the harmful fungi.

Examples of such preparations comprising the active compounds are:

I. A solution of 90 parts by weight of the active compounds and 10 parts by weight of N-methylpyrrolidone; this solution is suitable for use in the form of microdrops;

II. A mixture of 20 parts by weight of the active compounds, 80 parts by weight of xylene, 10 parts by weight of the adduct of 8 to 10 mol of ethylene oxide to 1 mol of oleic acid N-monoethanolamide, 5 parts by weight of the calcium salt of dodecylbenzenesulfonic acid, 5 parts by weight of the adduct of 40 mol of ethylene oxide to 1 mol of castor oil; a dispersion is obtained by finely distributing the solution in water;

III. An aqueous dispersion of 20 parts by weight of the active compounds, 40 parts by weight of cyclohexanone, 30 parts by weight of isobutanol, 20 parts by weight of the adduct of 40 mol of ethylene oxide to 1 mol of castor oil;

IV. An aqueous dispersion of 20 parts by weight of the active compounds, 25 parts by weight of cyclohexanol, 65 parts by weight of a mineral oil fraction of boiling point 210 to 280° C., and 10 parts by weight of the adduct of 40 mol of ethylene oxide to 1 mol of castor oil;

V. A mixture, ground in a hammer mill, of 80 parts by weight of the active compounds, 3 parts by weight of the sodium salt of diisobutylnaphthalene-1-sulfonic acid, 10 parts by weight of the sodium salt of a lignosulfonic acid from a sulfite waste liquor and 7 parts by weight of pulverulent silica gel; a spray mixture is obtained by finely distributing the mixture in water;

VI. An intimate mixture of 3 parts by weight of the active compounds and 97 parts by weight of finely divided kaolin; this dust comprises 3% by weight of active compound;

VII. An intimate mixture of 30 parts by weight of the active compounds, 92 parts by weight of pulverulent silica gel and 8 parts by weight of paraffin oil which had been sprayed onto the surface of this silica gel; this formulation imparts good adhesion to the active compound;

VIII. A stable aqueous dispersion of 40 parts by weight of the active compounds, 10 parts by weight of the sodium salt of a phenosulfonic acid/urea/formaldehyde condensate, 2 parts by weight of silica gel and 48 parts by weight of water; this dispersion may be diluted further;

IX. A stable oily dispersion of 20 parts by weight of the active compounds, 2 parts by weight of the calcium salt of dodecylbenzenesulfonic acid, 8 parts by weight of fatty alcohol polyglycol ether, 20 parts by weight of the sodium salt of a phenolsulfonic acid/urea/formaldehyde condensate and 88 parts by weight of a paraffinic mineral oil.

USE EXAMPLE

The synergistic activity of the mixtures according to the invention can be demonstrated by the following experiments:

The active compounds, separately or together, are formulated as a 10% emulsion in a mixture of 63% by weight of cyclohexanone and 27% by weight of emulsifier, and diluted with water to the desired concentration.

Evaluation is carried out by determining the infected leaf areas in percent. These percentages are converted into efficacies. The efficacy (W) is calculated as follows using Abbot's formula:

$$W=(1-\alpha/\beta)\cdot 100$$

α corresponds to the fungal infection of the treated plants in % and

β corresponds to the fungal infection of the untreated (control) plants in %

An efficacy of 0 means that the infection level of the treated plants corresponds to that of the untreated control plants; an efficacy of 100 means that the treated plants were not infected.

The expected efficacies of the mixtures of the active compounds were determined using Colby's formula [F. S. Colby, Weeds 15, 20–22 (1967)] and compared with the observed efficacies.

Colby's formula:

$$E=x+y-x\cdot y/100$$

E expected efficacy, expressed in % of the untreated control, when using the mixture of the active compounds A and B at the concentrations a and b x efficacy, expressed in % of the untreated control, when using active compound A at a concentration of a y efficacy, expressed in % of the untreated control, when using active compound B at a concentration of b.

Use Example 1

Activity Against Mildew of Wheat

Leaves of potted wheat seedlings cv. "Kanzler" were sprayed to runoff point with an aqueous preparation of active compound which was prepared from a stock solution comprising 10% of active compound, 63% of cyclohexanone and 27% of emulsifier and, 24 h after the spray coating had dried on, dusted with spores of mildew of wheat (*Erysiphe graminis forma specialis tritici*). The test plants were subsequently placed in climatized chambers at 20–24° C. and 60–90% relative atmospheric humidity for 7 days. The extent of the development of the infection on the leaves was then determined visually.

The visually determined values for the percentage of infected leaf areas were converted into efficacies as % of the untreated control. An efficacy of 0 means the same degree of infection as in the untreated control, an efficacy of 100 means 0% infection. The expected efficacies for active compound combinations were determined using Colby's formula (Colby, S. R. "Calculating synergistic and antagonistic responses of herbicide combinations", Weeds, 15 (1967), 20–22) and compared with the observed efficacies.

The results of the tests are shown in Tables 1 and 2 below:

TABLE 1

| Ex. | Active compound | Conc. in ppm | Efficacy in % of the untreated control |
|---|---|---|---|
| 1C | without | (67% infected) | 0 |
| 2C | Compound II.79 | 1 | 55 |
|  |  | 0.25 | 55 |

TABLE 1-continued

| Ex. | Active compound | Conc. in ppm | Efficacy in % of the untreated control |
|---|---|---|---|
| 4C | Compound I.a (common name: fenpropimorph) | 0.25 | 55 |
| 5C | Compound I.b (common name: fenpropidin) | 0.25 | 55 |
| 6C | Compound I.c (common name: tridemorph) | 1<br>0.25 | 0<br>0 |

TABLE 2

| Ex. | Mixture according to the invention (conc. in ppm) | Observed efficacy | Calculated efficacy* |
|---|---|---|---|
| 7 | 0.25 ppm Ia + 0.25 ppm II.79 | 96 | 80 |
| 8 | 1 ppm Ic + 1 ppm II.79 | 85 | 55 |
| 9 | 0.25 ppm Ic + 0.25 ppm II.79 | 90 | 55 |
| 10 | 0.25 ppm Ib + 0.25 ppm II.79 | 93 | 80 |

*Calculated using Colby's formula

The test results show that, for all mixing ratios, the observed efficacy is higher than the efficacy which had been calculated beforehand using Colby's formula.

We claim:

1. A fungicidal mixture, comprising as active components
   a) a morpholine or piperidine compound I selected from the group of compounds Ia, Ib, and Ic

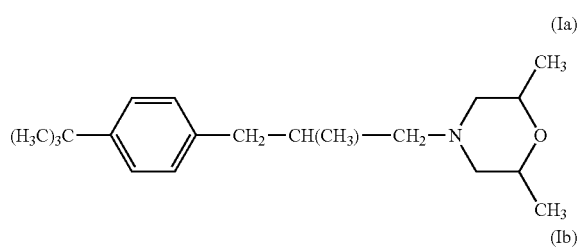

(Ia)

(Ib)

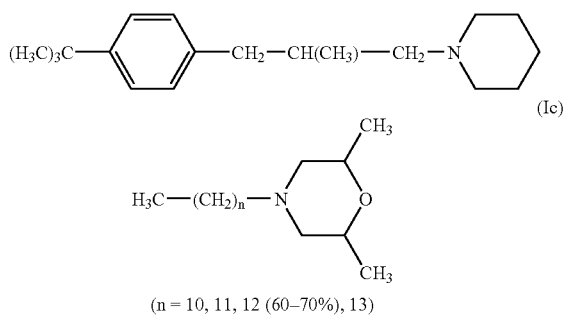

(Ic)

(n = 10, 11, 12 (60–70%), 13)

and b) a compound of formula II

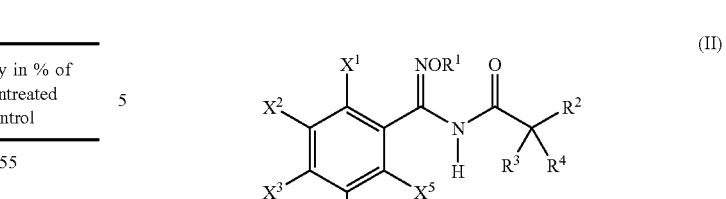

(II)

wherein
   $X^1$ is $C_1$-$C_4$-haloalkyl or $C_1$-$C_4$-haloalkoxy;
   $X^2$ is hydrogen or $C_1$-$C_4$-alkyl;
   $X^3$ is hydrogen or $C_1$-$C_4$-alkyl;
   $X^4$ is halogen;
   $X^5$ is halogen;
   $R^1$ is methylenecyclopropyl, methylenecyclopentyl, methylenecyclohexyl or methylenecyclohexenyl;
   $R^2$ is phenyl which is optionally substituted by halogen, $C_1$-$C_4$-alkoxy or $C_1$-$C_4$-alkyl;
   $R^3$ and $R^4$ are, independently of one another, hydrogen or $C_1$-$C_4$-alkyl; in a synergistically effective amount.

2. The mixture defined in claim 1, wherein $R^1$ is methylenecyclopropyl.

3. The mixture defined in claim 1, wherein $R^2$ is phenyl.

4. The mixture defined in claim 1, wherein $R^3$ or $R^4$ is hydrogen.

5. The mixture defined in claim 1, wherein $R^3$ and $R^4$ are hydrogen.

6. The mixture defined in claim 1, wherein $X^2$ or $X^3$ is hydrogen.

7. The mixture defined in claim 1, wherein $X^2$ and $X^3$ are hydrogen.

8. The mixture defined in claim 1, wherein $X^4$ is chlorine or fluorine.

9. The mixture defined in claim 1, wherein $X^5$ is chlorine or fluorine.

10. The mixture defined in claim 1, wherein
    $X^2$ is hydrogen;
    $X^3$ is hydrogen;
    $R^1$ is methylenecyclopropyl;
    $R^2$ is phenyl; and
    $R^3$ and $R^4$ are hydrogen.

11. The mixture defined in claim 1, which is conditioned in two parts, wherein one part comprises one or more compounds I in a solid or liquid carrier and the other part comprises one or more compounds of the formula II in a solid or liquid carrier.

12. A method for controlling harmful fungi, which comprises treating the fungi, their habitat or the materials, plants, seeds, soils, areas or spaces to be protected against fungal attack with the mixture defined in claim 1, where the compounds I and one or more compounds of formula II are applied simultaneously, that is either together or separately, or successively.

13. The mixture defined in claim 1, wherein in the compound of formula II
    $X^1$ is trifluoromethyl or difluoromethoxy;
    $X^2$ is hydrogen;
    $X^3$ is hydrogen;
    $X^4$ is chlorine or fluorine;
    $X^5$ is chlorine or fluorine;
    $R^1$ is methylenecyclopropyl;
    $R^2$ is phenyl; and
    $R^3$ and $R^4$ are hydrogen.

14. The method of claim 12, wherein in the compound of formula II
 $X^2$ is hydrogen;
 $X^3$ is hydrogen;
 $X^4$ is chlorine or fluorine;
 $R^1$ is methylenecyclopropyl;
 $R^2$ is phenyl; and
 $R^3$ and $R^4$ are hydrogen.

15. The method of claim 14, wherein in the compound of formula II
 $X^1$ is trifluoromethyl or difluoromethoxy; and
 $X^5$ is chlorine or fluorine.

16. The mixture defined in claim 1, which comprises the compound I and the compound of formula II in a ratio by weight of from 20:1 to 1:20.

17. The method of claim 12, wherein the compound I and the compound of formula II are applied in a ratio by weight of from 20:1 to 1:20.

18. The method of claim 12, wherein the mixture is applied in an amount of from 0.01 to 10 kg/ha.

19. The method of claim 12, wherein the mixture is applied to seeds in an amount of from 0.001 to 250 g/kg.

20. The method of claim 12, wherein the compound I is applied in an amount of from 0.01 to 2.5 kg/ha.

21. The method of claim 12, wherein the compound of formula II is applied in an amount of from 0.01 to 2 kg/ha.

* * * * *